United States Patent [19]

Gueret et al.

[11] Patent Number: 5,100,672

[45] Date of Patent: Mar. 31, 1992

[54] COMPOSITE FILM FOR SURFACE TREATMENT AND CORRESPONDING PROCESSES OF MANUFACTURE

[75] Inventors: Jean-Louis Gueret, Paris; Françoise Lebreton, Bures-sur-Yvette; Jean-Claude Contamin, Morangis, all of France

[73] Assignee: L'Oreal, Paris, France

[21] Appl. No.: 564,465

[22] Filed: Aug. 8, 1990

[30] Foreign Application Priority Data

Aug. 11, 1989 [FR] France .................. 89 10825

[51] Int. Cl.⁵ ............................................ A61F 13/00
[52] U.S. Cl. ............................... 424/449; 424/443; 424/448
[58] Field of Search .................... 424/448, 449, 443

[56] References Cited

U.S. PATENT DOCUMENTS

| | | | |
|---|---|---|---|
| 4,687,481 | 8/1987 | Nuwayser | 604/897 |
| 4,695,464 | 9/1987 | Alderman | 424/449 |
| 4,749,574 | 6/1988 | Ueda | 424/448 |
| 4,752,272 | 2/1988 | Gale | 424/448 |
| 4,784,857 | 11/1988 | Berry | 424/449 |

FOREIGN PATENT DOCUMENTS

| | | |
|---|---|---|
| 0137278 | 8/1984 | European Pat. Off. . |
| 0184910 | 11/1985 | European Pat. Off. . |
| 0196769 | 2/1986 | European Pat. Off. . |
| 0224981 | 7/1986 | European Pat. Off. . |
| 0289342 | 4/1988 | European Pat. Off. . |
| 0309309 | 8/1988 | European Pat. Off. . |
| 2100605 | 8/1982 | United Kingdom . |

*Primary Examiner*—Thurman K. Page
*Assistant Examiner*—D. Gabrielle Phelan
*Attorney, Agent, or Firm*—Cushman, Darby & Cushman

[57] ABSTRACT

The composite film according to the invention consists of an occlusive layer, and a reservoir layer consisting of a silicone polymer matrix containing a cosmetically and/or pharmaceutically active gelled aqueous phase in the form of dispersed inclusions, the whole being coupled with a removable protection. The matrix comprises a web on the side opposite the occlusive layer. This film can be applied to the skin to cause cosmetically or pharmaceutically active substances to enter via transcutaneous effects. The invention also relates to processes for the preparation of these films.

23 Claims, No Drawings

COMPOSITE FILM FOR SURFACE TREATMENT AND CORRESPONDING PROCESSES OF MANUFACTURE

The present invention relates to a composite film for local treatment of a surface, especially a region of skin, and to processes for the manufacture of the said film.

It is known to apply to skin films making it possible, by transcutaneous effects, to make pharmaceutical and/or cosmetic treatment products, especially water or aqueous solutions, enter the skin.

It has already been proposed, especially in European Patent Application EP-A-0,285,563, U.S. Pat. No. 4,923,517 to employ for this purpose composite films comprising a number of successive layers in the following order: a first, so-called occlusive, layer generally consists of a sheet of a substance which is impervious to the treatment products so as to prevent their evaporation and to facilitate the transcutaneous effects; a second layer, so-called reservoir layer, contains the treatment product(s): this layer is generally placed in contact with the skin and, to make it easier to attach the composite film to the skin, the reservoir layer is coated with a layer of adhesive substance which is permeable to the treatment products. Lastly, these composite films are often protected, while in storage, by a removable surface film which can be removed by peeling at the time of use and which is arranged on the opposite side to that where the occlusive layer is situated.

In these composite films attempts have been made to employ, as reservoir layer, a layer of silicone containing, in dispersion form, microdroplets of an aqueous phase, in particular of water. When the composite film is applied to the skin, the occlusive layer allows water to condense in the reservoir layer; the transfer of the water and of the other active substances present in the aqueous phase through the skin is thus made easier. Unfortunately, water evaporates rapidly out of such a reservoir layer and after a few hours has practically disappeared. It is therefore impossible to preserve and store these films. It has already been proposed to reduce the evaporation of water to a large extent by introducing into the silicone layer both the aqueous phase and at least one gelling agent for this aqueous phase (see, in this connection, EP-A-0,137,278). However, in the case of such films, when the reservoir layer is filled with a gelled aqueous phase dispersed in the polymer matrix, it has hitherto always been necessary to employ an adhesive layer to ensure the fastening of the film onto the skin for the treatment using transcutaneous effects. In fact, as soon as the quantity of gelled aqueous phase exceeds approximately 10% by weight in the reservoir layer it becomes practically impossible to produce a silicone polymer matrix which is self-adhesive by virtue of the partial nature of the polymerization of the silicone matrix and which, nevertheless, has a sufficient mechanical strength to prevent its breaking up into pieces while it is in use. Now, the use of an adhesive layer on the reservoir layer slows down the transcutaneous effects even if the adhesive is capable of allowing water to pass through and requires an additional stage in the process of manufacture, and this increases the prime cost of the product.

The Applicant proposes a composite film which makes it possible to avoid the abovementioned disadvantages. In this film the silicone polymer matrix contains up to 50% by weight of gelled aqueous phase relative to the total weight of the reservoir layer and it is only partially polymerized in order to provide it with its self-adhesive nature; its mechanical strength is ensured by virtue of a web which is included therein and which forms a reinforcement of the reservoir layer: the mesh opening of the web is sufficient not to interfere with the flow of the aqueous phase intended for the treatment to be carried out, but restricted enough to nevertheless form a barrier between the treated surface and the gel inclusions and thus to permit the self-adhesiveness of the matrix to the surface to be treated. The respective dimensions of the web, of the reservoir layer and of the gel inclusions are defined so that there should simultaneously be a good treatment effect, an easy handling and a sufficient self-adhesiveness of the composite film according to the invention.

The subject of the present invention is therefore a composite film for local treatment of a surface comprising, on the one hand, an occlusive layer and, on the other hand, a reservoir layer which encloses an active aqueous phase and is coupled to a removable protection, the reservoir layer consisting of a matrix made up of a silicone polymer inside which are arranged inclusions consisting of the active aqueous phase gelled by virtue of at least one gelling agent, characterized in that:

a) the silicone polymer matrix is only partially crosslinked, to be self-adhesive to the surface to be treated;

b) the gelled active aqueous phase represents from 10 to 50% by weight of the total weight of the reservoir layer;

c) the reservoir layer has a thickness of between 0.2 and 4 mm;

d) the mean size of the gelled active aqueous phase inclusions is chosen between 0.05 and 3 mm, this mean size being at most equal to the thickness of the reservoir layer;

c) the face of the reservoir layer which is opposite the occlusive layer carries a web reinforcing the said reservoir layer mechanically, the said web being included in the reservoir layer and defining meshes of mean size chosen between 0.01 mm and the mean size of the inclusions, the said web comprising from 10 to 1000 meshes per square centimetre and having a thickness of between 0.01 and 1.5 mm, the said thickness being at most equal to the thickness of the reservoir layer.

The presence of gelling agent in the aqueous phase slows down very markedly the evaporation of water out of the reservoir layer and the composite film prepared with this reservoir layer can be stored for a sufficient time in the common conditions of use. Moreover, in the presence of gelling agent it is possible to introduce a greater quantity of water into the reservoir layer. For example, in the presence of polyvinyl alcohol, 60% of water by weight can be introduced into the silicone matrix of the reservoir layer, whereas in the absence of gelling agent it is impossible to exceed 30% of water by weight. It is thought, although this explanation is not intended to constitute any kind of limit, that this increase in the quantity of aqueous phase which is stored stems from the fact that, if the cell of an inclusion is broken while the film is being handled, or opened as a result of its positioning at the edge of the reservoir layer, the aqueous phase does not flow out of the cell where it is present because of the gelling of the inclusions, and this reduces losses and prevents drying out of the reservoir layer starting at its edges.

In the present application a silicone polymer means linear organopolysiloxanes substituted on the Si atom by radicals chosen from the group consisting of $C_1$-$C_5$ alkyl, aryl or ar($C_1$-$C_2$ alkyl) radicals, the end silicon atoms being trisubstituted. Organopolysiloxanes of this type have been described especially in U.S. Pat. Nos. 2,541,137, 2,723,966, 2,863,846, 2,890,188, 2,927,907, 3,002,951 and 3,035,016.

In a preferred embodiment of the composite film according to the invention the surface treated using the said film is a region of skin and the active aqueous phase contains at least one cosmetic and/or pharmaceutical agent.

The aqueous phase may consist of water or of a water/propylene glycol mixture. It may also be a solution in water of at least one water-soluble cosmetically and/or pharmaceutically active substance. The aqueous phase may also consist of an emulsion or a dispersion of a water-insoluble product, for example an oil, which may contain liposoluble active substances. Among the water-soluble or liposoluble cosmetically and/or pharmaceutically active substances which can be introduced into the aqueous phase there may be mentioned, no limitation being implied;

cellular oxygenation factors such as D-panthenol, spleen extract, guanosine, thymus peptides, oligoelements;

regenerating, nourishing and/or cicatrising agents such as hydroxyproline, yeast extracts, placenta extracts, growth factors, centella asiatica, embryo extracts and other biological extracts and cerebrosides, sphingoceryls or other lipids of ceramide type;

firming agents such as monomethylsilanol lactate, mannuronates, trimethylsilanol and lady's mantle;

film-forming and/or tensive products such as amniotic fluid, serum albumin and horse serum;

hydrating products such as glycerine, urea, sodium lactate, mucopolysaccharides, amino acids, hyaluronic acid, filagrinol, chitin and chitosan derivatives, peptides, DNA, collagen, elastin;

water-soluble vitamins such as vitamins C, B2, H, panthenol, B6, PP, folic acid, magnesium 2-ascorbylphosphate;

liposoluble vitamins or their derivatives such as vitamins A, E, F, vitamin A palmitate, retinol;

antiinflammatory agents such as glycyrrhetinic acid, alpha-bisabolol, allantoin, palmityl collagenic acid or acetylsalicylic acid;

plant extracts, for example of ivy, of alga, of birch, of ruscus or butcher's-broom, of ginko biloba, of ginseng, of horsetail or of aloe;

bleaching agents such as hydroquinone or kojic acid;

and of various other specific agents such as xanthic bases like caffeine, alpha-tocopherol nicotinate, methyl nicotinate, menthol, camphor, asiatic acid, escin, alicyclic acids or thioxolones.

The gelling agent is preferably a gelling agent which swells in water. Among the gelling agents which can be employed according to the invention there may be mentioned natural substances such as starches, natural resins, (guar gum, gum arabic, gum tragacanths), casein, phytocolloids (carragenates, alginates, agar) and, preferably, gelatine:

semisynthetic cellulose derivatives such as carboxymethyl cellulose;

synthetic polymers such as polyvinyl alcohol; water-soluble vinyl polymers, for example the products sold by Goodrich under the trademark Carbopol and, preferably, the superabsorbent crosslinked polyacrylates with a high swelling ratio in water, for example the products marketed by Norsolor under the trademark Aqua Keep.

The silicone matrix contains aqueous phase inclusions in dispersed form. The size of the inclusions is controlled by acting on the stirring used for mixing the ingredients during the process for the manufacture of the reservoir layer.

The reservoir layer also contains, in a known manner, a catalyst for crosslinking the silicone.

In addition, the reservoir layer may contain dispersed hydrophilic particles of plant or mineral origin; these particles may be fibres or grains of powder. The reservoir layer may contain up to 50% by weight of hydrophilic particles relative to the weight of the silicone polymer. The advantage of the introduction of the hydrophilic particles into the matrix of the reservoir layer is that this promotes, by capillarity, the outflow of the aqueous phase which is responsible for the treatment of the surface onto which the film according to the invention is applied.

According to the invention the reservoir layer contains an imputrescible web which reinforces the said layer mechanically. This web consists of a sheet of perforated plastic material, of a perforated nonwoven, or of a woven net, the nonwoven or the net consisting of natural or synthetic fibres. It consists, for example of a polyamide net as described in FR-A-2,620,914.

The reservoir layer can be prepared by mixing, with stirring, the already gelled active aqueous phase into an uncrosslinked silicone polymer. It can also be prepared by mixing, with stirring, an uncrosslinked silicone, the active aqueous phase and the gelling agent. Mixing with stirring is carried out either between 1° and 5° C. to avoid an onset of crosslinking of the silicone polymer, or at room temperature, or also at a temperature at which the gelling agent is in the liquid state. The mixture intended to form the reservoir layer contains a crosslinking catalyst and the said mixture is heated to a temperature of between 25° and 150° C. for a period of between 1 min and 120 min. The quantity of crosslinking catalyst and the heating are chosen so as to obtain an incomplete crosslinking of the silicone of the reservoir layer so that it may benefit from a satisfactory self-adhesiveness.

In addition to the reservoir layer defined above, the composite film according to the invention also comprises an occlusive layer. The said occlusive layer is preferably a sheet of thermoplastic material with or without elastomer, in particular a sheet of polyvinyl chloride, of a copolymer of ethylene and vinyl acetate, of polyethylene, of polyester or of polyurethane. This sheet may be quilted or microperforated. It is preferably given a "nonslip" treatment to improve the adhesiveness between the occlusive layer and the reservoir layer. It is particularly advantageous to choose to produce the occlusive layer by means of a sheet of polyethylene, and this is possible, given that the silicone polymer matrix is sufficiently little crosslinked to be self-adhesive: the advantage in the use of polyethylene stems from the fact that this material has a good water-imperviousness, so that, when stored, the composite film according to the invention exhibits no drying out of the reservoir layer, provided that the latter is suitably protected on the side opposite the occlusive layer.

According to a first embodiment, the removable protection of the composite film according to the invention is a removable protective surface film which covers the reservoir surface on the face opposite the occlusive layer. According to another embodiment, the removable protection coupled with the composite film according to the invention is a receptacle containing the active aqueous phase, the subassembly consisting of the occlusive layer and the reservoir layer being immersed in the said receptacle to obtain the film which can be used for the treatment, the reservoir layer of the said subassembly comprising, before its introduction into the receptacle, only inclusions consisting of gelling agents carrying no active aqueous phase.

In the case where the reservoir layer is protected by a removable or peelable protective surface film, this surface film protects the said reservoir layer during the storage and the various handling operations on the product; it is removed at the time of use. This protective surface film can consist of a sheet of silicone-treated paper or of a sheet of thermoplastic material treated so as to make it antiadhesive, for example with the aid of a varnish. According to particularly preferred embodiment, the protective surface film is made of polyethylene, as is the occlusive layer. In such a case, arrangements are made for the protective surface film to have a thickness greater than that of the occlusive layer so as to be more rigid in order to ensure an easier separation at the time when the product is brought into use. This separation is all the easier since the protective surface film bears on the reservoir layer on the side where the web of the reservoir layer is situated, and this reduces the area of adhesiveness of the protective surface film to the self-adhesive silicone polymer matrix. It has been found that particularly satisfactory results were obtained when the occlusive layer had a thickness of between 0.01 and 0.1 mm and when the protective surface film had a thickness of between 0.05 and 0.3 mm, the thickness of the protective surface film being inclusively between 1.5 times and 3 times the thickness of the occlusive layer.

In a known manner, the composite film according to the invention can be cut out along a suitable contour corresponding to the surface region to be treated; the edges of the said contour are then preferably compressed to expel most of the reservoir layer and to bring the occlusive layer and the protective surface film substantially into contact. In the case where the occlusive layer has a thickness which is smaller than the protective surface film, as has already been indicated above, the compression gives rise to a preferential distortion of the occlusive layer, given that the protective surface film is more rigid; it follows that the product has a planar application face, that is to say that the edges of the occlusive layer are situated substantially in the same plane as the face of the reservoir layer which comes into contact with the skin: this results in a feeling of comfort on application and an improvement in the external insulation of the treated region, and this promotes the production of a transcutaneous effect.

In the case of the application to the human body, the composite film according to the invention can, in a known manner, be cut out in the form of a mask for application to the face, in the form of a half-ring for application to the bust, and in the form of a disc or any other form needed for application to a specified region of the body.

According to an advantageous embodiment, the silicone polymer containing its inclusions, a crosslinking catalyst and, optionally, other additives, is kept continuously stirred in a hopper at a temperature of 50° to 60° C. The mixture is delivered with the aid of a pump or of a tap, in front of a doctor blade under which the removable protective surface film and the web pass, each originating, for example, from a roll. The occlusive layer sheet also originating from a roll, is arranged to come on top, before calendering; the thickness of the reservoir layer which has been preformed by the doctor blade upstream is controlled by passing under a calender. The composite film obtained then runs through a hot air tunnel in which the temperature and the speed of passage of the composite film are adjusted so as to obtain a suitable polymerization time.

To obtain a product consisting of a composite film according to the invention a first process may be employed, for example, according to which the web of the reservoir layer is arranged on the protective surface film, the mixture made up of the silicone polymer comprising its gelled aqueous phase inclusions is coated onto this assembly, the sheet constituting the occlusive layer is placed on the layer thus formed, the composite film is cut out so that its edges have a contour corresponding to the surface region to be treated, the edges of the cut-out film are compressed to expel, in the compression region, most of the mixture constituting the reservoir layer, and the product is heated to cause the partial crosslinking of the silicone polymer of the reservoir layer.

According to another process, however, a gelling agent consisting of a superabsorbent crosslinked polyacrylate in the nonhydrated state is introduced and dispersed into the silicone polymer of the reservoir layer, this mixture is coated onto the sheet constituting the occlusive layer, the web of the composite film is placed in position, the partial crosslinking of the silicone polymer of the reservoir layer is produced and the film thus obtained is immersed in an active aqueous phase contained in a receptable, the said receptacle constituting the protection of the composite film.

EXAMPLE 40 g of an aqueous solution containing 10% by weight of D-panthenol are added to 2 g of polyacrylate powder (product marketed under the trade name "Aqua-Keep 10 SHNP" marketed by Norsolor). Slow mixing is performed by means of a stirrer with perforated blades. 100 g of organopolysiloxane (sold by Dow Corning under the trade name "Silastic MDX 4-4210 medical grade") are then added. 6 g of "Silastic MDX 4-4210 medical grade curing agent" catalyst sold by Dow Corning are added with stirring at 1000 revolutions/min and stirring is continued for 10 min.

Homogenized in this way, the product is spread into a layer 0.5 mm in thickness on a polyethylene sheet 0.2 mm in thickness. The surface of this protective surface film has been pretreated with a silicone oil to reduce its adhesiveness. Before the coating, a web consisting of a polyamide net comprising approximately 20 meshes/cm$^2$, which has a mean mesh size of 0.4 mm and a thickness of 0.1 mm, is placed in position on the protective surface film.

Above the coating is placed a polyethylene film (without slip treatment) 0.04 mm in thickness, which constitutes the occlusive layer, and this assembly is heated to 90° C. for 3 min in a ventilated oven.

After cooling, a composite film is thus obtained, comprising an occlusive layer and a reservoir layer made up of a matrix of partially polymerized silicone polymer, the whole being provided with a protective surface film which, on being removed, allows the silicone polymer matrix to adhere to the skin. The protective surface film is removed without any difficulty; after use, the film is separated without any difficulty from the skin to which it was applied; these two results are due to the reinforcement formed by the web of the reservoir layer, this being achieved despite the low degree of polymerization of the silicone polymer matrix.

The composite film is cut into pieces of desired size and is applied, using a gentle pressure, to the affected regions of the skin, for example to dermatitis or to burns. This composite film is preferably applied in the evening, the agents being released during the night, and the spent matrix is removed in the morning.

We claim:

1. Composite film for local treatment of a surface comprising, an occlusive layer and, a reservoir layer which encloses an active aqueous phase and is coupled to a removable protection, the reservoir layer consisting of a matrix made up of a silicone polymer inside which are arranged inclusions consisting of the active aqueous phase gelled by virtue of at least one gelling agent, wherein:
   a) the silicone polymer matrix is only partially crosslinked, to be self-adhesive to the surface to be treated;
   b) the gelled active aqueous phase represents from 10 to 50% by weight of the total weight of the reservoir layer;
   c) the reservoir layer has a thickness of between 0.2 and 4 mm;
   d) the mean size of the gelled active aqueous phase inclusions is chosen between 0.05 and 3 mm, this mean size being at most equal to the thickness of the reservoir layer;
   e) the face of the reservoir layer which is opposite the occlusive layer carries a web structurally reinforcing the said reservoir layer, the said web being included in the reservoir layer and defining meshes of mean size chosen between 0.01 mm and the mean size of the inclusions, the said web comprising from 10 to 1000 meshes per square centimeter and having a thickness of between 0.01 and 1.5 mm, the said thickness being at most equal to the thickness of the reservoir layer.

2. Film according to claim 1, characterized in that the surface treated using the said film is a region of skin, and that the active aqueous phase contains at least one cosmetic and/or pharmaceutical agent.

3. Film according to claim 2, characterized in that the gelled aqueous phase consists of a product taken from the group made up of water, a water/propylene glycol mixture, an aqueous solution of at least one cosmetically and/or pharmaceutically active water-soluble substance, and an emulsion or a dispersion in water of a water-insoluble cosmetically and/or pharmaceutically active substance.

4. Film according to claim 3, in which the gelled aqueous phase is an emulsion or a dispersion in water of a water-insoluble active substance, characterized in that the said water-insoluble active substance is an oil which may contain liposoluble agents.

5. Film according to claim 1, characterized in that the gelling agent is an agent which swells in the presence of water.

6. Film according to claim 5, characterized in that the gelling agent is a natural substance, a synthetic cellulose derivative or a synthetic polymer.

7. Film according to claim 6, characterized in that the gelling agent is gelatine.

8. Film according to claim 6, characterized in that the gelling agent is a superabsorbent crosslinked polyacrylate.

9. Film according to claim 1, characterized in that the matrix made up of a silicone polymer contains dispersed hydrophilic particles of plant or mineral origin.

10. Film according to claim 9, characterized in that the hydrophilic particles are fibres or grains of powder.

11. Film according to either of claims 9 and 10, characterized in that the matrix made up of a silicone polymer contains up to 50% by weight of hydrophilic particles relative to the weight of the silicone polymer.

12. Film according to claim 1, characterized in that the removable protection which is coupled with it is a removable protective surface film which covers the reservoir layer on its face opposite the occlusive layer.

13. Film according to claim 12, characterized in that the occlusive layer and the protective surface film are made up of a sheet of thermoplastic polymer, with or without elastomer.

14. Film according to claim 13, characterized in that the thermoplastic polymer is chosen from the group made up of polyvinyl chloride, copolymers of ethylene and vinyl acetate, polyethylenes, polyesters and polyurethanes.

15. Film according to claim 14, characterized in that the occlusive layer and the protective surface film both consist of a polyethylene sheet.

16. Film according to claim 15, characterized in that the occlusive layer has a thickness of between 0.01 and 0.1 mm and that the protective surface film has a thickness of between 0.05 and 0.3 mm, the thickness of the protective surface film being between 1.5 times and 3 times the thickness of the occlusive layer.

17. Film according to claim 15, characterized in that it is cut out according to the shape of the surface region to be treated, the edges of the said film having been compressed to expel most of the reservoir layer and to bring the occlusive layer and the protective surface film substantially into contact.

18. The film as claimed in claim 1, wherein said removable protection comprises a receptacle containing the active aqueous phase, said occlusive layer and said reservoir layer being immersed in said receptacle to thereby obtain the film to be employed for the treatment, said reservoir layer comprising only inclusions comprising gelling agent without any active aqueous phase.

19. Film according to claim 1, wherein the web of the reservoir layer comprises a perforated plastic material.

20. Film according to claim 1, wherein the web of the reservoir layer comprises a perforated net.

21. The film according to claim 20, wherein the net is nonwoven.

22. The film according to claim 19, wherein the net comprises natural fibers.

23. The film according to claim 19, wherein the net comprises synthetic fibers.

* * * * *